United States Patent [19]

Stackhouse et al.

[11] Patent Number: 4,810,269
[45] Date of Patent: Mar. 7, 1989

[54] POINT ONE MICRON FILTERING SYSTEM

[75] Inventors: Wyman H. Stackhouse, Manhattan Beach; Ian M. Williamson, Redondo Beach, both of Calif.

[73] Assignee: Stackhouse Associates, Inc., Ed Segundo, Calif.

[21] Appl. No.: 187,002

[22] Filed: Apr. 27, 1988

[51] Int. Cl.⁴ .................. B01D 27/06; B01D 46/10
[52] U.S. Cl. .................................. 55/267; 55/274; 55/276; 55/319; 55/356; 55/471; 55/472
[58] Field of Search .................... 55/267–269, 55/274, 276, 319, 385 R, 471–473, 356

[56] References Cited

U.S. PATENT DOCUMENTS

| | | | |
|---|---|---|---|
| 1,030,933 | 7/1912 | Smith | 55/276 X |
| 1,031,151 | 7/1912 | Smith | 55/276 X |
| 2,823,762 | 2/1958 | Bunnell | 55/276 |
| 3,925,043 | 12/1975 | Matrone et al. | 55/276 |
| 4,302,224 | 11/1981 | McCombs et al. | 55/276 X |
| 4,531,956 | 7/1985 | Howorth | 55/276 X |
| 4,560,395 | 12/1985 | Davis | 55/276 |
| 4,563,943 | 1/1986 | Bertelsen | 55/472 X |
| 4,701,193 | 10/1987 | Robertson et al. | 55/276 X |
| 4,737,173 | 4/1988 | Kudirka et al. | 55/276 |
| 4,762,540 | 8/1988 | Ruiz et al. | 55/276 |

FOREIGN PATENT DOCUMENTS

| | | | |
|---|---|---|---|
| 615359 | 7/1935 | Fed. Rep. of Germany | 55/276 |
| 2745406 | 4/1979 | Fed. Rep. of Germany | 55/276 |
| 2836708 | 2/1980 | Fed. Rep. of Germany | 55/276 |
| 3429633 | 2/1986 | Fed. Rep. of Germany | 55/276 |
| 76220 | 6/1981 | Japan | 55/276 |
| 1060885 | 12/1983 | U.S.S.R. | 55/276 |

*Primary Examiner*—Robert Spitzer
*Attorney, Agent, or Firm*—Singer & Singer

[57] ABSTRACT

A portable and mobile multi-stage filtering system is disclosed capable of filtering particulate of the size of one micron. An external canister filter capable of filtering down to at least 0.5 microns is connected to and located external to the cabinet of the airtight filtering system. The cabinet contains a centrally located high speed motor driving a high capacity vacuum pump completely surrounded by thermal and acoustical insulation. The air filtering path includes a plurality of baffles defining a serpentine path for exhausting the air into a series of plenums of increasing volume which communicates with a ULPA filter capable of filtering down to 0.12 micron. The plenums are also surrounded by acoustical and thermal insulation which has the effect of lowering the noise of the filtering system and increasing the efficiency of the total system.

13 Claims, 4 Drawing Sheets

POINT ONE MICRON FILTERING SYSTEM

This invention relates to a portable mobile submicron filtering system, and more particularly to a laser smoke filtration system capable of removing all laser smoke constituents including viable micro-organisms down to a previously unobtainable size of 0.12 microns and at an efficiency rating of 99.999%.

This invention was conceived primarily to protect operating personnel such as doctors, dentists and the like, who are using laser technology in operating room environments which places the operating personnel in the presence of micro-organisms that could seriously effect the health and safety of all personnel in the area.

The value of laser technology has become increasingly more valuable to the medial profession in such fields as gynecology, cervical dysplasia, venereal warts, endometriosis, fallopian tube procedures and vulvectomys.

In the field of dermatology, laser procedures have been used to remove stains, tattoos, treat fungal conditions, and also the removal of birth marks. Lasers are also being used in podiatry for fungal nails, plantars warts, bunionectomys, and neuroma removal. Brain tumors are also being removed by lasers in neurosurgery, and lasers have been used in endotracheal growth vaporization, and for the removal of carcinoma of the larynx in the pulmonary field.

Unfortunately, the use of laser surgery is also accompanied by the generation of large amounts of smoke and heat from irradiated tissues. In a study conducted by the Department of Otolaryngology and Public Health of Kurume University, Kurume, Japan, it was found that when there was complete vaporization of one gram of tissue, smoke particles were fifty-two times higher than the environmental standards regulated by their government agencies.

It would appear therefore, that without special protective measures being taken during operating room procedures using laser surgery, that pollution and smoke induced by laser irradiation could rise to an unacceptable level.

During laser surgery, operating room personnel are also concerned with being exposed to the HPV virus (human papillosa virus) which is presently in epidemic form in this country.

It is well known that when utilizing laser surgery, the intense heat destroys the molecules being treated, and that the virus attached to the molecules are immediately dispersed throughout the air thereby presenting a hazard to the operating personnel in the immediately vicinity.

The present invention is predicated on the principle that a virus by itself does not free-float in air and that an HPV virus has a diameter of approximately 0.045 micron or 45 nanometers in size. For virus to be viable it has to attach itself to a cell or a fragment of a cell in order to exist.

The present invention will filter and trap fragments as small as 0.12 micron. In this way operating room personnel using laser surgery techniques are protected from contact with harmful HPV virus and any other virus that may attach to a DNA cell or fragment of a cell.

There is disclosed a portable mobile vacuum filtering system having a plurality of stages of filtration for detecting and trapping particulates roughly the size of 0.1 micron.

It is necessary for systems of this type to be small and portable, and they must be extremely powerful to develop the necessary suction flow for the plurality of filters necessary to perform the 0.1 micron filtration, and last but not least, the system must be quiet and efficient since by necessity it is located within the operating room where the doctors and other operating personnel are working.

The invention comprises a multi-stage filtering process consisting of a canister filtering cartridge for filtering out smoke and larger size particulates feeding a self-contained structure containing an ULPA (Ultra Low Penetration Air) filter.

The central cabinet section contains a thermally and acoustically insulated centrally located high speed motor connected to and driving a high capacity vacuum pump.

The ULPA filter is located within an airtight structure, and is adapted to receive air from the pressure side of the vacuum pump. A plurality of acoustically insulated baffles are located within the airtight structure between the vacuum pump and the ULPA filter and forms a serpentine path for the filtered air from the vacuum pump to the ULPA filter. A plurality of air exhaust ports are located in the airtight structure in close proximity to the discharge area of the ULPA filter for exhausting filtered air back to the room atmosphere.

The system is used by having an operator or nurse hold a flexible hose having an open end which is maintained in close proximity to the source of particulate being generated by the laser activity. The other end of the flexible hose is connected to a filter cartridge located outside the cabinet structure where it is easily accessible to be removed and destroyed without having to open the structure to access the ULPA filter.

A typical canister filter is usually rated at being approximately 99% efficient at 0.5 micron. A typical canister filter is shown and described in U.S. patent application Ser. No. 148,338 entitled "Laser Smoke Particulate-Odor Filter System" invented by the same inventors of the present invention and assigned to the same assignee.

The other end of the disposable canister filter is connected by means of a second flexible tube to the vacuum side of the high capacity vacuum pump located in the structure.

In operation, the disposable canister filter which is external to the cabinet structure provides a pre-filtering action and is easily disposable thereby providing odor control and particulate control of particulates having a size of approximately 0.5 micron and in this way, protecting and extending the life of the 0.12 micron ULPA filter .

The acoustically insulated baffles provide a serpentine path for the filtered air path that acoustically reduces the sound level of the system and improves the efficiency of the ULPA filter. The serpentine paths of the baffles open the air path at each turn into an increasing larger size plenum chamber prior to reaching the ULPA filter. The net result is less acoustical noise, and a more efficient filtering action by the ULPA filter.

Increasing the volume of each plenum chamber reduces the velocity of the air and allows the volume of air in the filtering path to expand thereby reducing noise and improving the efficiency of the ULPA filter.

Further objects and advantages will be made apparent by referring now to the accompanying drawings wherein.

Figure 1:
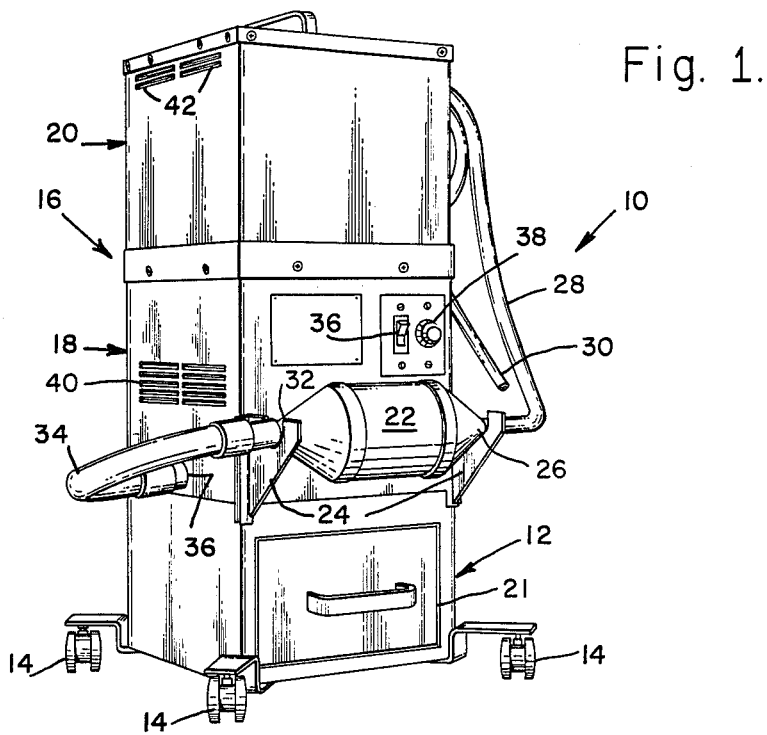
FIG. 1 is a perspective drawing of the complete multi-stage filtering system.

Referring now to FIG. 1, there is shown a complete self contained portable and mobile filtering system 10 comprising a lower storage portion 12 located on a plurality of casters 14 and an upper section 16 having a center portion 18 and an upper portion 20.

The lower portion 12 contains a storage area 21 suitable for holding additional filter canisters and other supplies.

The center portion 18 is fixedly attached to the upper cabinet 20 and holds an external filter canister 22 in a removal relationship by means of a pair of brackets 24.

One end 26 of canister 22 is connected to a flexible hose 28 having an end portion 30 that is adapted to be placed in close proximity to the particulate being captured and filtered. The other end 32 of canister 22 is connected to a second flexible tubing 34 which is connected to the vacuum end 36 of a high capacity vacuum pump located within the structure 18.

Structure 18 also contains suitable electrical controls such as an on/off switch 36 and a variable rheostat 38 together with louvers 40 for allowing cooling air to exit from within the structure 18. As will be described later in connection with FIGS. 4 and 5, the cooling air used to maintain thermal equilibrium of the motor and the pump is not mixed with the filtering air path of the air being filtered.

The upper portion 20 forming the upper case of the structure 16 contains a serpentine path for the filtering air path feeding the ULPA filter and is more fully described in connection with FIG. 2 of the accompanying drawings. The louvers 42 represent the discharge ports for the air filtering path of the air being filtered.

Figure 2:
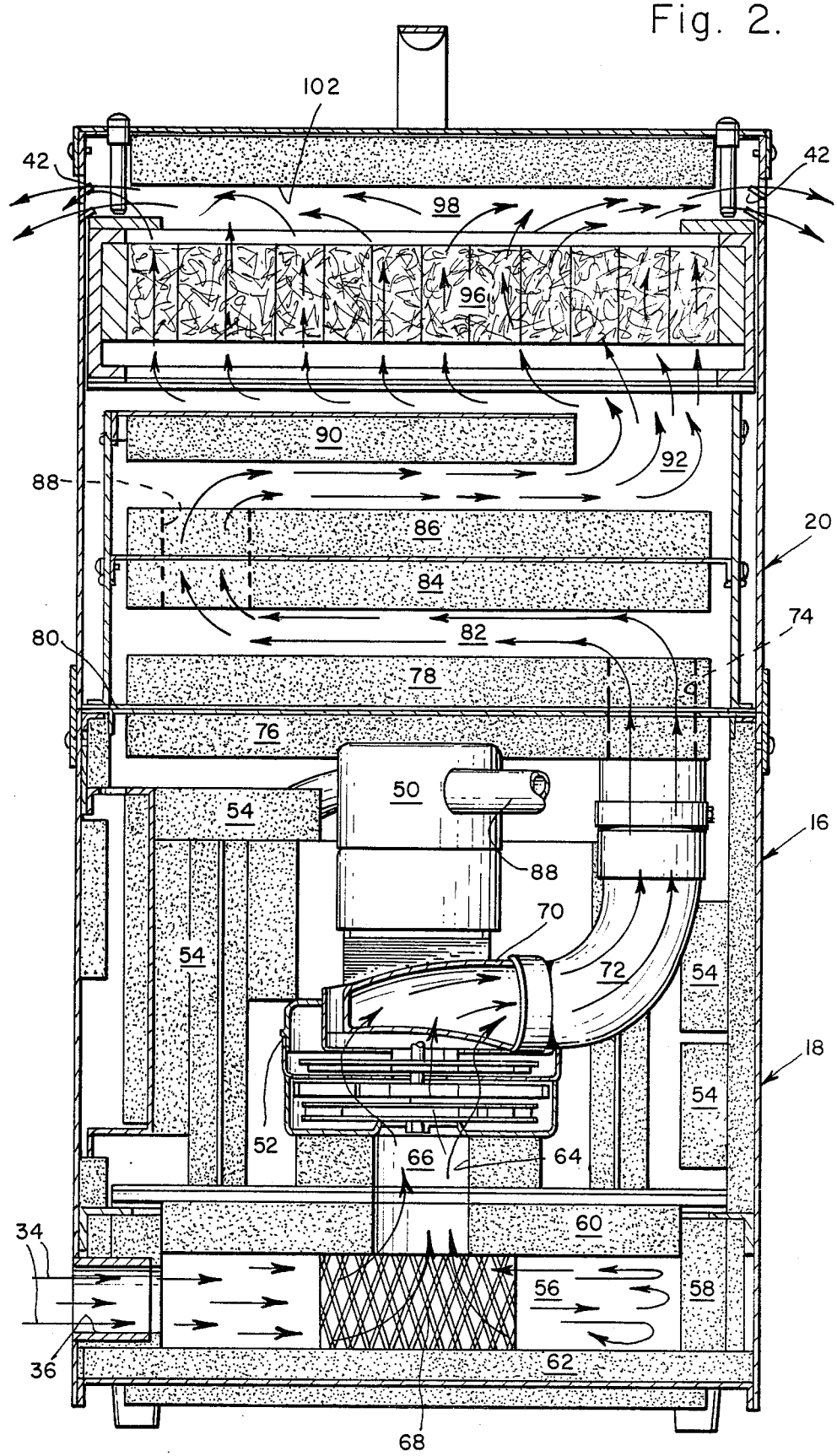
FIG. 2 is a cross-sectional view of the air filtering path within the structure.

Referring now to FIG. 2, there is shown a cross-sectional view of the structure 16 illustrated in connection with FIG. 1 illustrating the lower portion 18 and the upper portion 20. The flexible hose 34 is connected to the vacuum intake 36 located in the lowermost portion 16 which forms part of the filtering air path.

Located within the lower portion 18, is a centrally located high speed motor 50 mechanically connected to and driving a high capacity vacuum pump 52. The motor 50 and pump 52 are thermally and acoustically insulated within the lower portion 18 by means of acoustic baffles 54 that are located on the walls of the lower container 18 and around the pump and motor.

The filtering air path from the external flexible hose 34 is fed into a plenum chamber 56 which is formed on the sides by means of acoustical and thermal baffling 58 and on the top by means of baffling 60 and on the bottom by means of baffling 62. The vacuum side 64 of the pump 52 communicates with the plenum chamber 56 by means of a passage way 66 that terminates within the plenum chamber 56 thereby forming the filtering path. A screen 68 is located within the plenum chamber 56 in order to preclude accidental entry of gross foreign material into the vacuum portion 64 should the system be run without the external canister filter 22.

The pump 52 is a high capacity vacuum pump of the type necessary to draw a sufficient vacuum to produce the necessary high air velocity within the filtering air path. The acoustical and thermal filters 54, 58, 60, 62, 76, 78, 84, 86, 90, and 102 are necessary to reduce the noise of the driving motor 50 and pump 52 which is a direct result of the action of the high speed motor and pump and the fact that a substantially high velocity of air in the filtered air path is generated.

The requirement for a quiet filtering machine is necessary when it is considered that machines of this type are located in the operating rooms of hospitals and in other critical areas where surgery takes place.

In the preferred embodiment, a tangential high capacity vacuum pump 52 is used to generate the high capacity vacuum needed to filter the air in the filtering air path. Unfortunately pumps of this type are known as "screamers" because of the resulting noise they generate.

The pressure output side 70 of the pump 52 is fed through a suitable elbow 72 and through an opening 74 to a first set of baffles 76 and 78. The baffles 76 and 78 are located in the upper section 20 of the airtight structure 16 which is otherwise isolated from the lower portion 18 by means of a solid reenforcing plate 80 which serves the dual purpose of reenforcing the connecting structure between the lower portion and the upper portion and also physically separates the inside area of the upper portion 20 from the open area located within the lower portion 18. This function is very important since the volume within the lower portion contains cooling air necessary to maintain the thermal equilibrium of motor 50 and pump 52 and the cooling air and the air being filtered must always be kept separate. The cooling function will be described more fully in connection with FIGS. 4 and 5.

Figure 3:
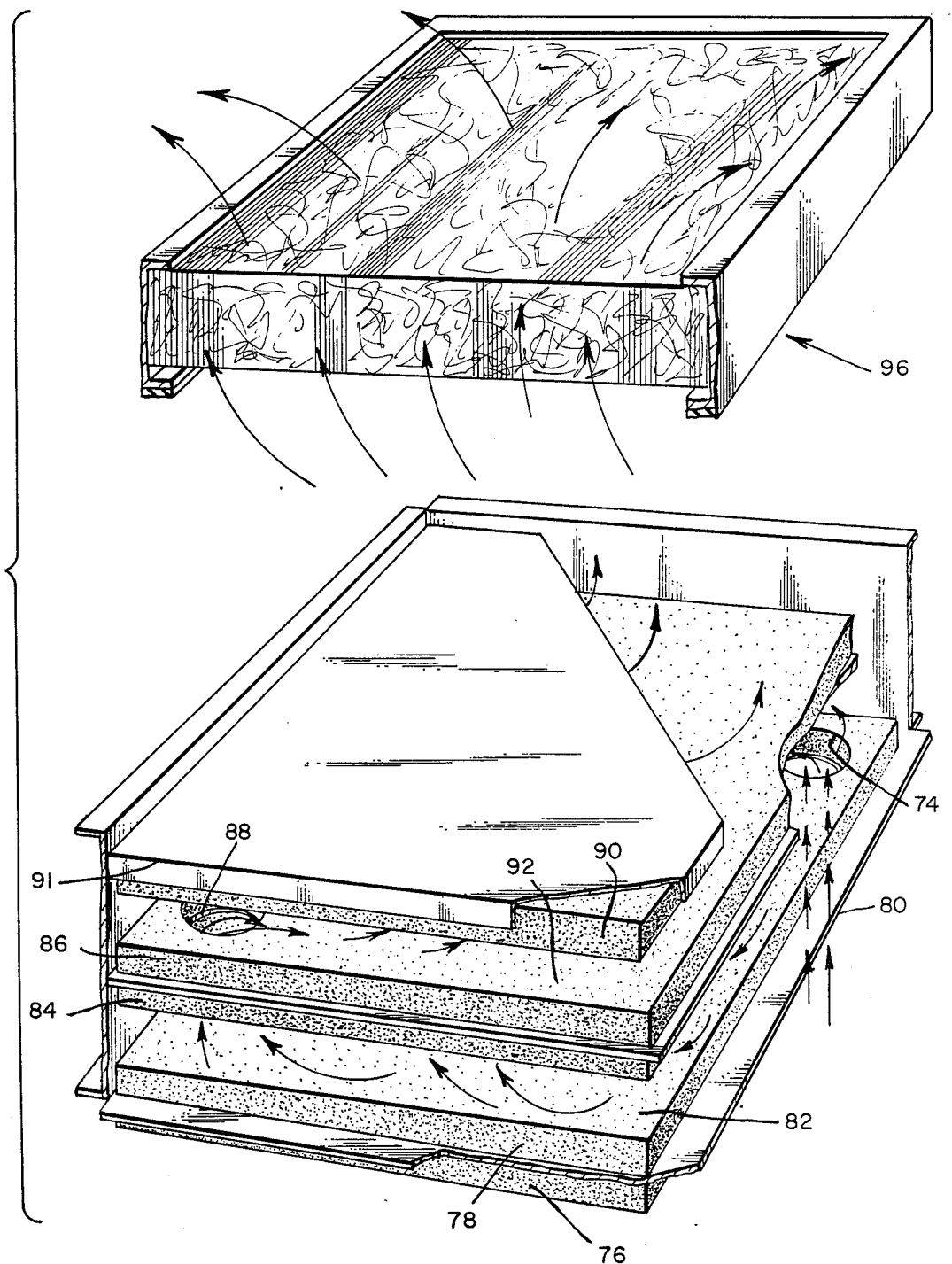
FIG. 3 is an exploded view of the air baffles and the ULPA filter illustrating the expansion chamber for the filtering air path.

In reviewing the baffles please refer also to FIG. 3 which illustrated in exploded form the operation of the baffles and the construction of the defined plenum areas. A review of baffles 76 and 78 will show that baffle 76 is located in the lower portion 18, whereas baffle 78 is located in the upper portion 20. The opening 74 is part of the filtering air path which allows the air being filtered to enter a plenum area 82 formed by an additional set of baffles 84 and 86. Baffles 84 and 86 also contain an opening 88 at a point on the baffles that is diagonally opposite the opening 74 located on baffles 76 and 78.

The filtering air path from the opening 74 into the plenum chamber 82 provides a plenum chamber of increased volume which causes a reduction in sound energy. A similar further reduction in sound energy is caused by the opening 88 feeding the plenum 92.

The filtering air path also defined as a serpentine path has the unobvious advantage of feeding the air to be filtered into acoustically lined plenum chambers of increased path length. This action causes a still further reduction in sound energy, and also permits a more efficient filtering action by the ULPA filter.

The filtering air path is again diverted by means of another baffle 90 which has a solid supporting member 91 located over the opening 88 positioned in baffles 84 and 86. The baffle 90 also defines still another plenum chamber 92 which has a progressively larger volume causing further reduction in sound energy and also reduces entering air velocity at the ULPA filter, optimizing service life of the ULPA filter. In the preferred embodiment, baffle 90 is cut at an angle thereby leaving approximately ⅔ of the original baffle in place. Located above baffle 90 is an ULPA filter 96 which completely encloses the filtering air path thereby forcing all air being filtered to pass through the ULPA filter. The ULPA filter 96 is the final stage in the filtration process and captures viable and nonviable particles in size down to 0.12 micron with an efficiency of 99.999%. The filtered air passing through filter 96 is exhausted into plenum chamber 98 formed by the upper portion of the ULPA filter 96 and acoustical and thermal barrier 102 which helps define the plenum chamber 98. Suitable louvers 42 located on the side portions of the upper cover 20 allow the filtered air to pass back into the room atmosphere.

By way of review, the filtered air path comprises the filter cannister 22, the flexible tube 34 feeding the plenum chamber 56 which communicates with the vacuum side of pump 52 which forces the air being filtered through an elbow 72 and through opening 74 into plenum 82, through opening 88 within baffles 84 and 86 and the plenum chamber 92 which communicates with ULPA filter 96 before allowing the filtered air to pass through the louvers 42 back into the atmosphere.

Referring again to FIG. 3, there is shown an exploded view more fully illustrating the baffles and the ULPA filter located within the upper chamber 20. Plate 80 is a complete barrier between the lower chamber 18 and the upper chamber 20. The opening 74 is shown within the lower baffle 76 and the upper baffle 78 thereby allowing the filter air path to extend within the plenum chamber 82. The hole 88 located within baffles 84 and 86 allows the air path to enter and expand within plenum chamber 92 where the air is free to enter and pass through the ULPA filter 96 before being exhausted into the atmosphere.

The serpentine path results from having openings 74 and 88 located in diametrically opposite corners thereby allowing the air being filtered to pass into plenums that increase in volume. It is known that plenums providing increasing cross-sectional area lower the noise level, and by decreasing the air velocity, improve the performance of the ULPA filter 96. In this manner, the filtration process is maintained and the noise is controlled within acceptable limits.

The use of the baffles located around the motor 50 and the pump 52 are used for acoustical control. The noise control measures require that cooling air be provided for maintaining the thermal equilibrium of the motor, the electrical controls and the pump.

Figure 5:
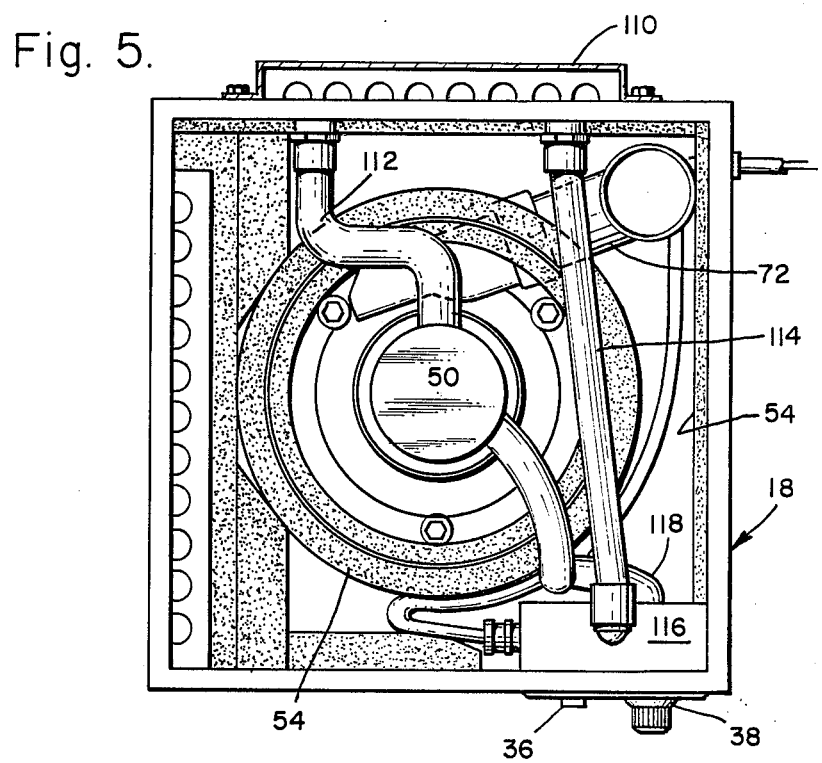
FIG. 5 is a plan view illustrating the separate cooling paths for cooling the high speed motor and electrical controls.
Figure 4:
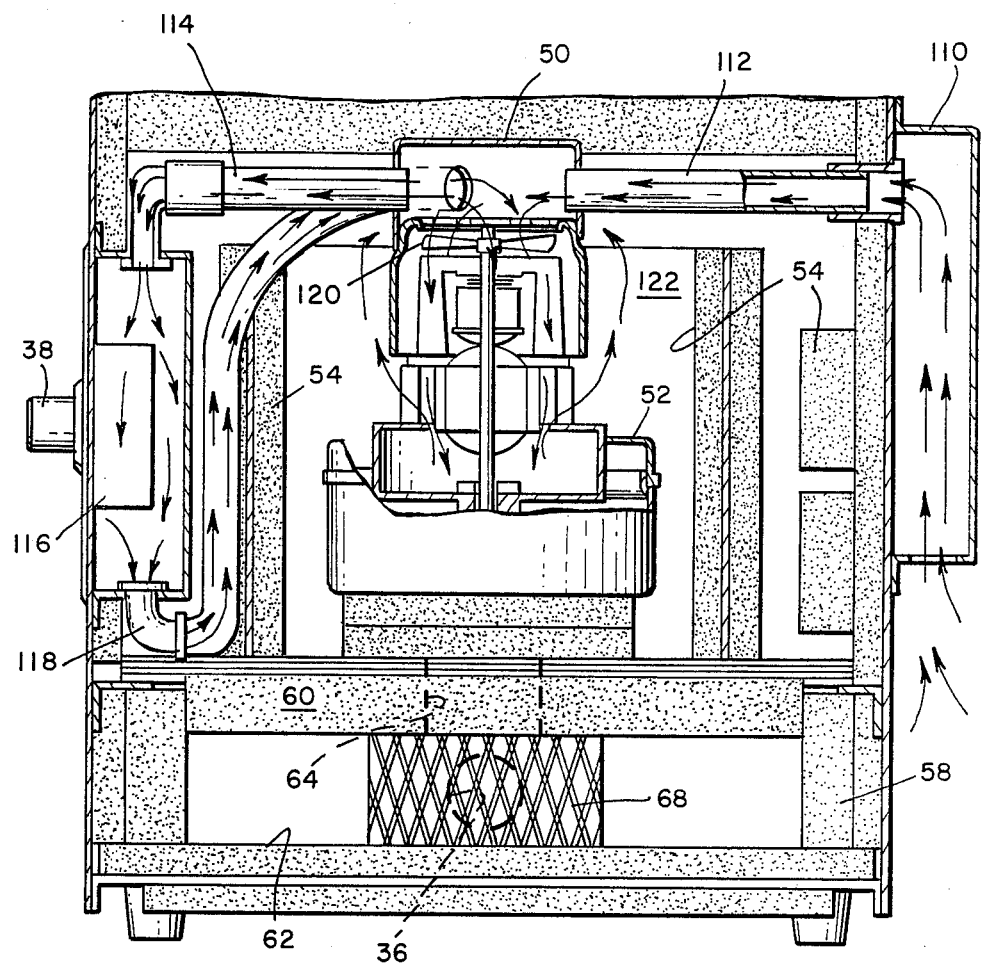
FIG. 4 is an elevational view of the high speed motor and high capacity vacuum pump and the separate cooling paths needed to maintain a stable thermal condition.

Referring now to FIGS. 4 and 5, there is shown a top view and an elevation view respectively of the lower portion 18 which more fully illustrates the cooling devices used to maintain the motor 50, the flow control device 38 and the pump 52 in thermal equilibrium.

By definition, a large capacity motor 50 is necessary to drive the high capacity vacuum pump 52 needed to create the vacuum necessary to cause movement of the air being filtered through the defined filters.

Motors of this size are commonly known as screamers because of the noise that they make when running at high RPM's. Since the equipment must operate in an environment where clear speech communication is essential, such as the operating room of a hospital, it is necessary that the complete system operate as quietly as possible and hence the need for thermal and acoustical insulation as described in connection with FIGS. 1, 2 and 3. Also, all electrical apparatus when operating at high power generates heat and in view of the enclosed environment of the motor 50 and pump 52 it is necessary to provide external cooling air to maintain the pump, motor, and electrical apparatus in thermal equilibrium.

Referring now to FIGS. 4 and 5, there is shown how fresh and cooling air is directed from an outside baffle 110 which pulls in fresh air through tubing 112 and directs this air to the top-most portion of motor 50.

A second cooling air intake port directs cooling air from the baffle 110 through a tube 114 that feeds air into a sealed electrical box 116 that contains the necessary electrical parts such as flow control device 38 and switch 36. The box 116 is completely sealed and the cooling air entering the box from tube 114 passes through the internal electrical components and is evacuated by means of tube 118 which is also connected to the top-most portion of the pump 50.

FIG. 4 more fully illustrates the fact that underneath the outer cover of motor 50 is fan impeller 120 directly driven by the electrical motor 50 which is used to create a suction for pulling air directly from tube 112 and from tube 118 thereby causing a flow of air directly into the motor from tube 112 and at the same time provides a vacuum for drawing air through the electrical box 116 through tube 114. The air is exhausted through the motor 50 into a plenum chamber 122 which is defined by insulation 54 that completely encompasses the motor 50 and the pump 52.

The plenum chamber 122 communicates with louvers 40 located on the side of lower cabinet 18 as more fully illustrated in FIG. 1. The louvers are not illustrated in FIG. 4 since they are on the far side of the cabinet. In this manner, the cooling air is directed only to the motor, the electrical components and the pump and then exhausted to the atmosphere without being contaminated with the air being filtered.

In operation, the filtering system is portable and mobile and is easily moved by the users to place the external hose in close proximity to the area where the particulate is being generated.

The pre-filter canister 22 being external to the over all system is easily removed and disposed of and has the effect of extending the life of the 0.12 micron ULPA final stage filter.

The unique design of the multi-stage filtering system allows the use of an ULPA filter to be used in a high capacity vacuum system and with a minimum of noise.

The best mode of constructing the invention has been described with the ULPA filter located on the pressure side of the pump. The benefits claimed for the invention can also be achieved by changing the path of the filtering air so that the ULPA filter is located on the vacuum side of the pump and only the suppressor system comprising the serpentine plenum chambers are located on the pressure side of the pump. In such a system a separate cooling air system would not be needed since the air from the pump would already be filtered and could be used to cool the motor and the pump directly thereby resulting in a simpler system.

We claim:

1. A self-contained portable and mobile filtering system comprising:

a self-contained structure containing a thermally and acoustically insulated, centrally located high speed motor connected to and driving a high capacity vacuum pump;

a filtering air path comprising said high capacity vacuum pump having a vacuum side and a pressure side for causing a high velocity air flow in said filtering air path;

an ULPA filter (ultra low penetration air) having a discharge area on one side and a second side located within said structure and connected with said vacuum pump to form part of said filtering air path;

a plurality of acoustically insulated baffles forming a serpentine air path located within said structure intermediate said vacuum pump and said ULPA filter and connected to form part of said filtering air path;

said baffles providing an expanding cross sectional area for attenuating noise generated by said vacuum pump and for lowering the velocity of the filtered air in said filtering air path from said pump to said ULPA filter;

a plurality of air exhaust ports in said structure located in the proximity of said discharge area of said ULPA filter for exhausting the low velocity filtered air passing through said ULPA filter.

2. A filtering system according to claim 1 which includes a screen located within said structure and connected to the vacuum side of said vacuum pump for preventing accidental entry of gross sized foreign material from entering said filtering air path.

3. A filtering system according to claim 1 in which the plurality of acoustically insulated baffles are sequentially located between the ULPA filter and the vacuum pump with a first portion of the baffle closest to the ULPA filter and in which said portion of the baffle closest to said ULPA filter is removed thereby exposing a larger cross sectional area in the space between the baffle and the ULPA filter for allowing the velocity of the air in the filtered air path to reduce.

4. A filtering system according to claim 3 in which the baffle closest to said ULPA filter is cut at almost a 45 degree angle and removed thereby exposing an increased area in said filtered air path.

5. A filtering system according to claim 1 which includes a flexible hose forming part of said filtering air path and having an open end adapted to be placed in close proximately to the source of particulate being filtered and a second end connected to the vacuum side of said vacuum pump.

6. A filtering system according to claim 5 which includes a filter cartridge external of said self contained structure and located in said filtering air path between said flexible hose and said vacuum pump for removing particulate larger than 0.5 micron.

7. A filtering system according to claim 1 which includes separate air cooling intake channels isolated and insulated from said filtering air path and connected to said high speed motor for maintaining said motor in a stable thermal condition; and separate air cooling exhaust ports for discharging said cooling air from said high speed motor outside of said structure.

8. A self contained portable and mobile filtering system according to claim 1 in which said ULPA filter is located in the filtering path on the high pressure end of said pump.

9. A self contained portable and mobile filtering system according to claim 1 in which said baffles are located between said pump and said ULPA filter.

10. A self contained portable and mobile vacuum filtering system comprising:

a self-contained air tight structure containing a thermally and acoustically insulated centrally located high speed motor connected to and driving a high capacity vacuum pump having a vacuum side and a pressure side;

an ULPA filter having a discharge side and located within said airtight structure and adapted to receive air from the pressure side of said vacuum pump;

a plurality of acoustically insulated baffles located within said structure between said vacuum pump and said ULPA filter for forming a serpentine air path for filtering air from the pump to said ULPA filter;

said vacuum pump, acoustically insulated baffles and said ULPA filter connected together to form said serpentine air path, and a plurality of air exhaust ports in said air tight structure located in the proximity of the discharge area of said ULPA filter for exhausting filtered air passing through said ULPA filter.

11. A self contained portable and mobile filtering system according to claim 10 which includes a flexible hose having a first end and a second end and forming a part of said filtering path and in which said first end is adapted to be placed in close proximity to the source of particulate being filtered; and a filter cartridge having a first end and a second end and located outside of said airtight structure capable of filtering larger size particulates connected to the other second end of said flexible hose and forming a part of said filtering air path; and in which said vacuum side of said vacuum pump is connected through a second flexible hose to the second end of said filter cartridge and forms a part of said filtering air path.

12. A self contained portable an mobile filtering system according to claim 10 which includes separate air cooling intake channels isolated and insulated from said filtering air path and connected to said high speed motor for maintaining said motor in a stable thermal condition; and separate air cooling exhaust ports for discharging said cooling air from said high speed motor outside of said structure.

13. A self contained portable and mobile filtering system according to claim 10 which includes a screen located within said airtight structure and connected to the vacuum side of said vacuum pump for preventing gross sized foreign material from entering said filtering air path.

* * * * *